United States Patent [19]
Knight et al.

[11] Patent Number: 6,017,549
[45] Date of Patent: Jan. 25, 2000

[54] NON-IRRITATING COSMETIC AND PHARMACEUTICAL COMPOSITIONS

[75] Inventors: E. Althea Knight, Teaneck, N.J.; Daniel H. Maes, Huntington; Carmen Castillo-Bucci, Greenlawn, both of N.Y.; Jules Zecchino, Closter, N.J.

[73] Assignee: E-L Management Corp., New York, N.Y.

[21] Appl. No.: 08/940,783

[22] Filed: Sep. 30, 1997

[51] Int. Cl.[7] .............................. A61K 6/00; A61K 7/00; A01N 25/32; A01N 37/18
[52] U.S. Cl. ................................ 424/401; 424/406; 514/2
[58] Field of Search ................................ 514/2; 424/401, 424/406

[56] References Cited

U.S. PATENT DOCUMENTS 5,395,620   3/1995   Huc et al. .............................. 424/499

FOREIGN PATENT DOCUMENTS

WO 92/06778   4/1992   WIPO .
9401088   1/1994   WIPO .............................. A61K 9/107

*Primary Examiner*—Avis M. Davenport
*Attorney, Agent, or Firm*—Dorene M. Price, Esq.; Karen A. Lowney, Esq.

[57] ABSTRACT

The present invention relates to a cosmetic or pharmaceutical emulsion for topical application to the skin comprising an irritating agent and at least one non-disruptive emulsifier. In a preferred embodiment the irritating agent is a retinoid. The invention also provides a method for decreasing the irritation on the skin caused by an irritating active agent in a topical cosmetic or pharmaceutical emulsion which comprises employing as an emulsifier at least one of an alkyl polyoside, a grafted water soluble protein on a hydrophobic backbone, and lecithin.

33 Claims, No Drawings

NON-IRRITATING COSMETIC AND PHARMACEUTICAL COMPOSITIONS

FIELD OF THE INVENTION

The invention relates to topically applied cosmetic and pharmaceutical compositions. In particular, the invention relates to cosmetic and pharmaceutical emulsions which are non-irritating when applied to the skin.

BACKGROUND OF THE INVENTION

It is a frequent complaint of users of certain types of topically applied products that they are irritating to the skin. This complaint is often associated with the emulsion-based products which typically utilize relatively large quantities of emulsifiers or surfactants to maintain the stability of the composition. Although there may be many reasons for this irritation, at least part of this problem may be connected with the action of the emulsifiers on the skin's native lipid barrier. The lipid barrier is a collection of varied lipids, such as triglycerides, ceramides, and free fatty acids, located in the stratum corneum. The barrier serves to prevent the penetration of most substances to the lower layers of the skin, as well as preventing water loss from the skin. Unfortunately, the very properties that make standard emulsifiers useful in maintaining a stable emulsion, i.e., the ability to couple hydrophilic and lipophilic materials, also potentially cause a disruption of the lipid barrier; this action in turn can permit more rapid penetration of any irritants that may be in the vicinity of the area where the barrier has been weakened. Thus, while the emulsifiers themselves are not necessarily irritants, their action on the skin can indirectly lead to irritation.

The problem is compounded when a topically applied emulsion contains an active or therapeutic component which is in itself irritating, even in the absence of emulsifiers. In such a case, the irritant is essentially being deliberately applied in combination with components which will almost certainly weaken the barrier, thereby permitting a rapid penetration of the irritant to the lower layers of the skin. This can potentially lead to a very significant level of discomfort to the user, which may cause the user to ultimately discontinue use of an otherwise therapeutically useful product.

The complete elimination of emulsifiers from topically applied products is difficult, if not impossible, to achieve, given the popularity and utility of emulsions as a delivery vehicle. However, as the foregoing discussion shows, their use in a composition with potentially irritating actives is problematical. Thus, there is a continued effort to find ways of formulating such actives without enhancing their irritation potential, and further, to reduce their irritation potential to levels which will be acceptable to the average user of the product. The present invention provides such formulations.

SUMMARY OF THE INVENTION

The present invention relates to cosmetic and pharmaceutical compositions comprising an emulsion containing at least one irritating active agent and at least one non-disruptive emulsifier. By "non-disruptive emulsifier" is meant one which has substantially no disruptive effect on the skin's lipid barrier. Emulsifiers of this type can be selected from the group consisting of an alkyl polyoside, a water soluble protein grafted to a lipid soluble aliphatic hydrocarbon backbone, and a hydrogenated lecithin, and mixtures thereof. The invention also relates to a method of reducing the irritancy of an active ingredient in a cosmetic or pharmaceutical formulation which comprises combining the active ingredient in an emulsion with a non-disruptive emulsifier. The invention is particularly useful in the preparation of retinoid- or hydroxy acid-containing formulations.

DETAILED DESCRIPTION OF THE INVENTION

It has now been unexpectedly discovered that certain types of emulsifiers are not only non-irritating when applied alone, but are also capable of reducing the irritating properties of an otherwise irritating dermatological agent when formulated together. The emulsifiers in question have been previously used in non-irritating formulations. However, they have not previously been used in combination with known irritating active agents. Further, their ability to actually reduce the irritant index of an irritating agent on the skin has not previously been recognized. Particularly surprising is the observation that, not only do the emulsifiers of the invention not strip the lipid barrier, they also appear to actively enhance the barrier properties. While not wishing to be bound by any particular theory, it is believed that the efficacy of these emulsifiers in substantially preventing or significantly reducing irritation caused by an irritating agent is related to this enhancement; the enhanced barrier properties may significantly delay penetration of the irritant, thereby slowing down the development of irritation.

It has been discovered that there are a number of different types of known emulsifiers which are capable of enhancing the barrier function. One group which is useful for this purpose is alkyl polyosides, which are well known and widely used commercially. The preferred emulsifiers of this type contain a $C_{12-22}$ alkyl portion, preferably $C_{12-18}$, which may be straight-chain or branched, and at least one sugar moiety such as glucose, mannose, fructose, maltose, dextrose, saccharose, galactose, lactose, ribose, xylose, allose, cellulose, maltotriose, and the like. Methodology for production of such alkyl polyosides are disclosed in WO92/06778, the contents of which are incorporated herein by reference. A particularly preferred alkyl polyoside is cetearyl glucoside. Alkyl polyosides can be used in an amount of about 0.5–10%, preferably from about 2–7% by weight of the composition.

A second type of emulsifier which has similar properties are grafted water soluble proteins on an aliphatic hydrocarbon backbone. The aliphatic backbone preferably has a chain length of $C_{12-36}$, preferably $C_{14-22}$. A number of different types of these products are available commercially, for example wheat protein stearate or oat protein stearate. These materials can be used in an amount of from about 0.5–10%, preferably about 2–5%, by weight of the total composition.

A third type of emulsifier useful in the emulsions of the invention are lecithin derivatives. Particularly preferred are hydrogenated lecithins, more preferably hydrogenated lecithins with a phosphatyl choline level of between about 30–60%. The amount of lecithin used can be from about 0.5–5% by weight of the total composition.

Any one of the types of emulsifiers noted above can be used alone, or in any combination, to achieve the desired result. In a particularly preferred embodiment, the emulsion contains at least one of each type of emulsifier, with a concurrent reduction, preferably at least about 20%, in the quantity of each component used.

The emulsifiers can be used to reduce the irritant index of virtually any irritating active agent to be applied topically. An irritating material, for purposes of the present specification and claims, is one which, when applied in therapeutically effective amounts to skin in a standard emulsion or in a typical solvent, routinely produces an irritant index of about 1.5 or greater in the Kligman Chamber Scarification Test (Frosch and Kligman, Contact Dermatitis 2: 314–324, 1976). Among the dermatological irritants which can be rendered less irritating by combination with the noted emulsifiers are retinoids, for example, retinol, retinal, retinoic acid and derivatives of these compounds, for example, retinyl palmitate, retinyl acetate and the like; alpha- and beta-hydroxy acids, such as lactic, glycolic, citric, alpha-hydroxyoctanoic, alpha-hydroxydecanoic, alpha-hydroxylauric, and salicylic acids, and derivatives thereof; Vitamin C(ascorbic acid) and its derivatives, resorcinol, benzoyl peroxide, lactamides and quaternium ammonium lactates. It will of course be apparent that the emulsions of the invention can contain more than one irritant material, for example, a combination of a retinoid and Vitamin C or a derivative thereof. The therapeutically effective amounts of any of these active materials are well-established in the art.

In a particularly preferred embodiment, the dermatological agent is a retinoid. By retinoid in the present context is meant Vitamin A(retinol) and any natural or synthetic analogues of Vitamin A which qualitatively exhibit the same type of activity as Vitamin A on the skin. Example of retinoids, in addition to retinol include, but are not limited to, Vitamin A acid, Vitamin A aldehyde, and Vitamin A esters. The retinoids have a wide variety of dermatological applications, including the general retardation of the effects of aging, both normal and photoaging. More specific application includes prevention and reduction of wrinkles, skin atrophy, hyperpigmentation and abnormal epidermal growths. Retinoids have also proven useful in the treatment of acne. Although they are quite valuable therapeutic agents, the retinoids have historically been difficult to formulate in way which is sufficiently non-irritating to the user to permit repeat applications, such as are needed to achieve their optimum therapeutic effect. However, the present formulations succeed in reducing the irritant index of retinoids to a level which is acceptable to the consumer. In particular, the present invention provides retinoid compositions which have an irritant index, according to the Kligman chamber scarification test, in the range of about 0.8–1.25, depending on the other components of the formulation, which places the formulations within the same irritant level range as a saline solution. In contrast, for example, a typical retinol-containing formulation, without the non-disruptive emulsifiers, can normally have an irritant index as high as 1.7 or more. Thus, in a preferred embodiment of the present invention, the non-disruptive emulsifiers are used in an emulsion containing a retinoid active agent, in an amount of from about 0.001–5%, preferably about 0.001–2%, by weight of the total composition, the amount and regimen for application depending on the contemplated use of the retinoid.

In an additional embodiment, the irritating agent of choice can be encapsulated to further reduce the level of irritation caused. In a preferred example of this embodiment the irritating agent is encapsulated in microcapsules comprising a matrix containing collagen and a glycosaminoglycan. In particular, the irritating agent is encapulated in microcapsules such as disclosed in U.S. Pat. No. 5,395,620, the contents of which are incorporated herein by reference. Such microcapsules are also available under the name Thalaspheres® from Bioetica, Inc., Portland, Me.

While not so limited, in a preferred embodiment, the emulsion of the invention is an oil-in-water emulsion. The aqueous phase may be any cosmetically acceptable water based material, such as deionized water, or a floral water. The oil phase may be any cosmetically or pharmaceutically acceptable oil, such an oil being defined for the present purpose as any pharmaceutically or cosmetically acceptable material which is substantially insoluble in water. The oils may be volatile or non-volatile, or a mixture of both. For example, suitable volatile oils include, but are not limited to, both cyclic and linear silicones, such as cyclomethicone, octamethylcyclotetrasiloxane, and decamethylcyclopentasiloxane; or straight or branched chain hydrocarbons having from 8–20 carbon atoms, such as decane, dodecane, tridecane, tetradecane, and C8–20 isoparaffins.

Non-volatile oils include, but are not limited to, di- or triglycerides, vegetable oils, such as coconut oil, jojoba oil, corn oil, sunflower oil, palm oil, soybean oil; carboxylic acid esters such as isostearyl neopentanoate, cetyl octanoate, cetyl ricinoleate, octyl palmitate, dioctyl malate, coco-dicaprylate/caprate, decyl isostearate, myristyl myristate; animal oils such as lanolin and lanolin derivatives, tallow, mink oil or cholesterol; glyceryl esters, such as glyceryl stearate, glyceryl dioleate, glyceryl distearate, glyceryl linoleate, glyceryl myristate; non-volatile silicones, such as dimethicone, dimethiconol, dimethicone copolyol, phenyl trimethicone, methicone, simethicone; and nonvolatile hydrocarbons, such as isoparaffins, squalane, or petrolatum.

The emulsions may also comprise other optional components, depending on the intended end use. These include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like.

The invention is further illustrated by the following non-limiting examples.

EXAMPLES

Example I

A composition according to the present invention is prepared as follows:

| Material | Weight % |
| --- | --- |
| Phase I | |
| Deionized water | 51.00 |
| Wheat Protein Stearate [Bioetica] | 0.70 |
| Disodium EDTA | 0.10 |
| Sucrose | 2.00 |
| Caffeine Powder | 0.20 |
| Phase II | |
| BHT | 0.10 |
| Isostearyl Neopentanoate | 3.00 |
| Squalane | 3.00 |
| Cetearyl glucoside | 5.00 |

-continued

| Material | Weight % |
| --- | --- |
| Shea butter | 5.90 |
| Phase III | |
| Cyclomethicone | 7.00 |
| Phase IV | |
| Carbomer | 0.50 |
| Deionized water | 9.50 |
| Phase V | |
| Glycerine | 2.00 |
| Green tea extract | 1.00 |
| 1,3 Butylene Glycol | 1.50 |
| Deionized water | 1.50 |
| Phase VI | |
| Triethanolamine | 0.05 |
| Deionized water | 1.95 |
| Phase VII | |
| Magnesium ascorbyl palmitate | 0.35 |
| Deionized water | 3.00 |
| Phase VIII | |
| Vitamin E | 0.40 |
| Phase IX | |
| Oil soluble green tea extract | 0.15 |
| Retinol (50% in soybean oil) | 0.10 |

To prepare the composition, Phase I components are combined in the main vessel and heated to 80° C. The Phase II ingredients are combined in an auxiliary vessel and heated to 82° C. Phase I and Phase II ingredients are then combined under homomixing and side-swipe agitation. Phase III ingredients are added to the main vessel at 65° C. Phase V and Phase IV ingredients are added sequentially to the main vessel at 50° C., and each mixed until uniform. Phase VI ingredients are added to the main vessel at 40° C. and mixed until uniform. Phase VII ingredients are added at 38° C. and mixed until uniform. Phase VIII ingredients are added at 35° C. and mixed until uniform, and then Phase IX added at 30° C., and mixed until uniform.

Example II

A composition according to the present invention, containing retinol as the active agent, is tested in the Kligman Chamber Scarification Test, to determine the level of irritancy of the composition.

A panel of 10 individuals is selected to participate in the test. The volar surface of panelists' forearms are examined to ensure there is no gross pathology. On day 1, the skin is cleansed with alcohol and a 1 cm diameter site is outlined. The skin of each site is then scratched with the sharp beveled edge of a sterile 30 gauge needle. Four closely spaced equidistant parallel strokes are made horizontally and four vertically in cross-hatch fashion. Sufficient pressure is applied to cleave the superficial layers of skin without eliciting frank capillary bleeding. Each site is covered with a chamber containing webril pads which have been moistened with 0.08 ml of sterile physiological saline. The chambers are moored tightly to the site with a wide strip of Hypafix® tape.

After four hours the chambers are removed and the skin is examined. Inflammation, if detected, is graded on a scale of 1–4 in accordance with the intensity of the effect, 0 being no change on the site, and 4 being inflammation showing on all of the contact area, or any portion thereof if accompanied by papular blister formation. These results establish a baseline for each individual's responsiveness.

After determining baseline, chambers containing 0.08 ml of a retinol product containing cetearyl glucoside, wheat protein stearate, and hydrogenated lecithin are applied and affixed to the designated sites. Each panelist is asked after 30 minutes to record any sensations of pain or discomfort, and then instructed to return 24 hours later.

On each of days 2 and 3, the panelists' arms are examined and graded according to the aforementioned scale, and new chambers are applied. On day 4, the sites are examined to determine if there has been any change in condition of the treated site. The overall grades are calculated for each panelist. The possible irritant indices are : 0–0.4(low), 0.5–1.4(slight), 1.5–2.4(moderate), and marked(2.5–4.0). The test composition of the invention, in which the retinoid is not encapsulated, produces a score of 1.25; when the retinoid is encapsulated, in same testing scenario, the score is about 0.85. Each of these scores fall within the same irritancy range as saline, which, when tested simultaneously, receives scores of from about 0.5–0.8, thereby showing a very favorable irritant index for the formula of the invention.

What we claim is:

1. A topically applied cosmetic or pharmaceutical emulsion for reducing the irritation properties of an irritating agent comprising the irritating agent in combination with at least one non-disruptive emulsifier.

2. The emulsion of claim 1 in which the emulsifier is selected from the group consisting of alkyl polyosides, a grafted water soluble protein on a hydrophobic backbone, and lecithin.

3. The emulsion of claim 1 in which the emulsifier is a cetearyl glucoside.

4. The emulsion of claim 1 in which the emulsifier is a wheat protein stearate.

5. The emulsion of claim 1 in which the emulsifier is a hydrogenated lecithin.

6. The emulsion of claim 1 in which the lecithin is a hydrogenated lecithin having a phosphatyl choline content of about 30–60%.

7. The emulsion of claim 1 which contains more than one of a non-disruptive emulsifier selected from the group consisting of an alkyl polyoside, a grafted water soluble protein on a hydrophobic backbone, and a lecithin.

8. The emulsion of claim 7 in which the lecithin is hydrogenated lecithin with a phosphatyl choline content of about 30–60%.

9. The emulsion of claim 1 in which the irritating agent is selected from the group consisting of retinoids, alpha- and beta-hydroxy acids and derivatives thereof; Vitamin C and derivatives thereof; resorcinol; benzoyl peroxide; lactamides; and quaternium ammonium lactates.

10. The emulsion of claim 1 in which the irritating agent is a retinoid.

11. The emulsion of claim 1 in which the irritating agent is retinol.

12. A cosmetic or pharmaceutical emulsion for reducing the irritation properties of a retinoid comprising the retinoid in combination with at least one non-disruptive emulsifier selected from the group consisting of alkyl polyosides, a grafted water soluble protein on a hydrophobic backbone, and lecithin.

13. The emulsion of claim 12 in which the retinoid is retinol and the emulsifier is at least one of cetearyl glucoside, wheat protein stearate, or hydrogenated lecithin.

14. The emulsion of claim 13 in which the hydrogenated lecithin has a phosphatyl choline content of about 30–60%.

15. The emulsion of claim 12 which comprises retinol, cetearyl glucoside, wheat protein stearate and hydrogenated lecithin.

16. The emulsion of claim 15 which comprises retinol in an amount of from about 0.001–2.0%, cetearyl glucoside in an amount of from about 0.5–10%, wheat protein stearate in an amount of from about 0.1–5.0%, and hydrogenated lecithin in an amount of from about 0.1–10%, each by weight of the total emulsion.

17. A method of decreasing the irritation on the skin caused by an irritating active agent in a topical cosmetic or pharmaceutical emulsion which comprises employing as an emulsifier at least one of an alkyl polyoside, a grafted water soluble protein on a hydrophobic backbone, and lecithin.

18. The method of claim 17 in which the lecithin is a hydrogenated lecithin.

19. The method of claim 17 in which the lecithin is a hydrogenated lecithin having a phosphatyl choline content of about 30–60%.

20. The method of claim 17 in which the irritating agent is selected from the group consisting of retinoids, alpha- and beta-hydroxy acids and derivatives thereof; Vitamin C and derivatives thereof; resorcinol; benzoyl peroxide; lactamides; and quaternium ammonium lactates.

21. The method of claim 17 in which the irritating agent is a retinoid.

22. The method of claim 17 in which the irritating agent is retinol.

23. The method of claim 17 in which the emulsifier is selected from the group consisting of cetearyl glucoside, wheat protein stearate, and a hydrogenated lecithin.

24. The method of claim 17 in which the irritating agent is a retinoid and the emulsifier comprises one of each of an alkyl polyoside, a grafted water soluble protein on a hydrophobic backbone, and lecithin.

25. The method of claim 17 in which the irritating agent is retinol and the emulsifier comprises one of each of cetearyl glucoside, wheat protein stearate, and a hydrogenated lecithin having a phosphatyl choline content of about 30–60%.

26. An oil-in-water emulsion for reducing the irritation properties of a retinoid comprising the retinoid in combination with a non-disruptive emulsifier selected from the group consisting of alkyl polyosides, a grafted water soluble protein on a hydrophobic backbone, and a hydrogenated lecithin.

27. Emulsion of claim 26 in which the lecithin is a hydrogenated lecithin having a phosphatyl choline content of about 30–60%.

28. The emulsion of claim 26 which comprises retinol and at least one of cetearyl glucoside, wheat protein stearate, and a hydrogenated lecithin having a phosphatyl choline content of about 30–60%.

29. The emulsion of claim 26 in which the retinoid is encapsulated.

30. The emulsion of claim 26 in which the retinoid is encapsulated in a microcapsule comprising a matrix containing collagen and a glycosaminoglycan.

31. The emulsion of claim 30 which comprises each of cetearyl glucoside, wheat protein stearate, and a hydrogenated lecithin.

32. The emulsion of claim 31 which comprises retinol in an amount of from about 0.001–2.0%, cetearyl glucoside in an amount of from about 0.5–10%, wheat protein stearate in an amount of from about 0.1–5.0%, and hydrogenated lecithin in an amount of from about 0.1–10%, each by weight of the total emulsion.

33. The emulsion of claim 32 in which the lecithin has a phosphatyl choline content of about 30–60%.

* * * * *